(12) United States Patent
Cummins et al.

(10) Patent No.: US 9,801,400 B2
(45) Date of Patent: Oct. 31, 2017

(54) NATURAL HONEY-CONTAINING COMPOSITIONS AND METHOD OF PREPARATION

(75) Inventors: Nicholas James Cummins, Slough (GB); Jayant Eknath Khanolkar, Surbiton (GB); Vasiliki Poulopoulou, Bagshot (GB); Vaishali Shailendra Rane, Egham (GB)

(73) Assignee: The Procter & Gamble Company, Cincinnati, OH (US)

( * ) Notice: Subject to any disclaimer, the term of this patent is extended or adjusted under 35 U.S.C. 154(b) by 1607 days.

(21) Appl. No.: 12/135,243

(22) Filed: Jun. 9, 2008

(65) Prior Publication Data
US 2009/0017165 A1    Jan. 15, 2009

(30) Foreign Application Priority Data
Jun. 8, 2007    (EP) .................................... 07011294

(51) Int. Cl.
| | |
|---|---|
| A23G 3/00 | (2006.01) |
| A23L 1/08 | (2006.01) |
| A61K 9/00 | (2006.01) |
| A61K 31/137 | (2006.01) |
| A61K 31/167 | (2006.01) |

(Continued)

(52) U.S. Cl.
CPC ................ *A23L 1/08* (2013.01); *A23L 21/25* (2016.08); *A23L 29/06* (2016.08); *A23L 29/262* (2016.08); *A61K 9/0095* (2013.01); *A61K 31/137* (2013.01); *A61K 31/167* (2013.01); *A61K 31/4748* (2013.01); *A61K 47/12* (2013.01); *A61K 47/38* (2013.01); *A61K 47/46* (2013.01); *C12Y 302/01004* (2013.01); *A23V 2002/00* (2013.01)

(58) Field of Classification Search
CPC .......................................................... A23L 1/09
USPC ................................................... 426/656, 103
See application file for complete search history.

(56) References Cited

U.S. PATENT DOCUMENTS 5,024,996 A *  6/1991  Ringe ............................ 514/54
5,200,218 A *  4/1993  Lasater et al. .................. 426/72
(Continued)

FOREIGN PATENT DOCUMENTS

| CN | 1 067 159 A | 12/1992 |
|---|---|---|
| CN | 1 927 164 A | 3/2007 |
| RU | 1788886 A3 * | 1/1993 |

OTHER PUBLICATIONS

Kunieda: Carbohydrate metabolism genes and pathways in insects: insights from the honey bee genome; Insect Molecular Biology (2006) 15 (5), 563-576 © 2006; Journal compilation © 2006 The Royal Entomological Society 563.*

(Continued)

*Primary Examiner* — Patricia A George
(74) *Attorney, Agent, or Firm* — Amanda Herman; Alexandra S. Anoff; Kelly Lynn McDow

(57) ABSTRACT

Compositions comprising cellulosic polymers and natural honey that display reduced instability due to the presence of a chelant that inhibits the activity of naturally occurring cellulases are described. Methods of treating natural honey to inhibit cellulase activity comprising mixing the natural honey with a chelant and optionally heating the mixture are provided. Flavor compositions consisting of natural honey and a chelant, optionally in a carrier are further described.

31 Claims, 1 Drawing Sheet

(51) Int. Cl.
*A61K 31/4748* (2006.01)
*A61K 47/12* (2006.01)
*A61K 47/38* (2006.01)
*A61K 47/46* (2006.01)
*A23L 29/00* (2016.01)
*A23L 29/262* (2016.01)
*A23L 21/25* (2016.01)

(56) References Cited

U.S. PATENT DOCUMENTS

| | | | |
|---|---|---|---|
| 6,132,758 A * | 10/2000 | Munayyer et al. | 424/439 |
| 6,284,502 B1 * | 9/2001 | Maenz et al. | 435/168 |
| 6,319,513 B1 * | 11/2001 | Dobrozsi | 424/434 |
| 2006/0141031 A1 * | 6/2006 | Nelson et al. | 424/464 |
| 2007/0134299 A1 * | 6/2007 | Giles | 424/440 |

OTHER PUBLICATIONS

Indian Child: http://web.archive.org/web/20030702133326/http://indianchild.com/bees.htm; Jul. 2003.*

Sanford: Original Oral Chelation Formula #1; published Sep. 5, 2006 and Jan. 29, 2007; http://wayback.archive.org/web/20061201000000*/http://www.goldshieldelite.com/downloads/LT691WA.pdf.*

Wirich: A Study of the Enzymic Degradation of CMC and Other Cellulose Ethers; Journal of Polymer Science: Part A-1 vol. 6, 1965-1974 (1968).*

Babacan, Sibel et al., "Characterization of Honey Amylase," Journal of Food Science, vol. 72, No. 1, Jan. 2007, pp. C50-C55.

Babacan, S., et al., "Honey Amylase Activity and Food Starch Degradation," Journal of Food Science, vol. 67, No. 2, 2002, pp. 1625-1630.

European Search Report, dated Sep. 28, 2007.

* cited by examiner

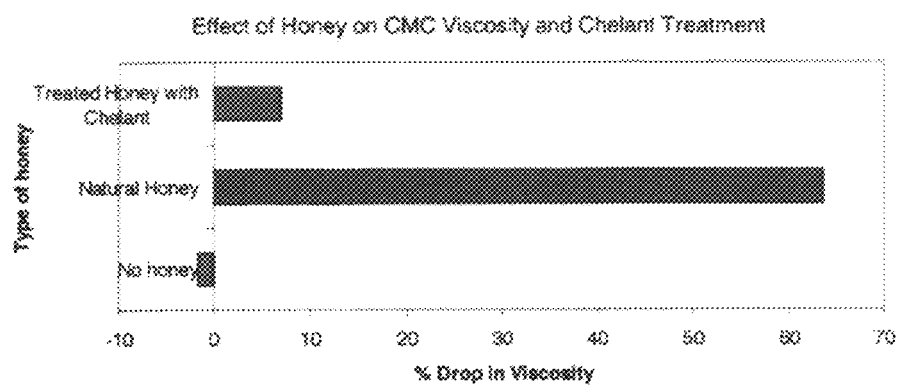

NATURAL HONEY-CONTAINING COMPOSITIONS AND METHOD OF PREPARATION

FIELD OF THE INVENTION

The present invention relates to flavour compositions comprising natural honey and a chelant and compositions comprising said flavour compositions and a cellulosic polymer. Processes of preparing the compositions of the present invention are also provided.

BACKGROUND OF THE INVENTION

Natural honey is a useful and important flavouring agent and possesses some medical and herbal benefits. Natural honey is becoming increasingly used in medicinal preparations, as well as food and beverage compositions. The stability of these compositions when comprising natural honey may be affected as a result of the constituents of the natural honey itself. For example, natural honey has been shown to have a starch (amylose and amylopectin) degradation effect due to the presence of amylase, an enzyme that cleaves the α1-4 linkage between glucose units (Babacan, S. et al, (2002) *Honey Amylase Activity and Food Starch Degradation* 67(5), pp 1625-1630).

The present inventors have found that when natural honey is used in a composition comprising a cellulosic polymer, as opposed to starch-based molecules, degradation of the cellulosic polymer can be observed. This degradation was not associated with amylase activity in the natural honey, as amylase does not impact cellulosic polymers to a significant extent. The present inventors identified the presence of cellulase enzymes in natural honey as the cause of the degradation of the cellulosic polymers. Cellulase is previously unreported as being present in natural honey. Although it is common to refer to mixture of compounds that can degrade cellulose as cellulase it is really composed of more than one enzymes, including β-1-4-glucanase and β-glucosidase (see the schematic below).

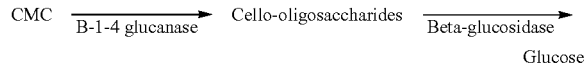

The use of natural honey in combination with cellulosic polymers resulted in a lack of stability of the final composition, generally identified as a loss of viscosity of the formulation. Therefore, a need exists for compositions and flavours comprising natural honey and methods of preparation such that, when used in combination with cellulosic polymers, the natural honey does not result in degradation of cellulosic polymers and subsequent compositional instability.

SUMMARY OF THE INVENTION

The present invention provides a honey composition consisting essentially of:
a) natural honey comprising at least one cellulose enzyme; and
b) a chelant.
Furthermore, the present invention provides a composition comprising;
a) natural honey comprising at least one cellulose enzyme;
b) a chelant; and
c) a cellulosic polymer.
Further still, the present invention provides a process for the manufacture of a composition comprising natural honey comprising the step of mixing a chelant with natural honey comprising at least one cellulose enzyme and optionally a carrier. The compositions and methods of preparation provide natural honey containing compositions that have improved stability.

BRIEF DESCRIPTION OF THE DRAWINGS

FIG. 1 demonstrates the loss of viscosity associated with the degradation of carboxymethylcellulose sodium in a system comprising natural honey and the inhibition of said polymer degradation and viscosity loss when using chelants treatment.

DETAILED DESCRIPTION OF THE INVENTION

As used herein, all percentages are weight percentages unless otherwise indicated. All temperatures are in degrees Celsius (° C.) unless otherwise indicated.

The present invention provides a honey composition consisting essentially of natural honey comprising at least one cellulose enzyme and a chelant. The honey composition may be formulated as a flavour composition by combining the natural honey and chelant with a carrier. Furthermore, the present invention provides for a composition comprising natural honey comprising at least one cellulose enzyme in combination with a chelant and a cellulosic polymer.

Natural Honey

The compositions, flavour compositions and processes of manufacture herein require the presence of natural honey. As used herein, the term "natural honey" includes honey produced by bees (*Apis mellifera* L.) or other insects from the nectar of plants or from secretions of living parts of plants which the bees collect, transform by combining with specific substances of their own, deposit, dehydrate, store and leave in the honey comb to ripen and mature. The natural honey must contain at least one cellulose enzyme The honey composition herein consisting essentially of natural honey and a chelant contains natural honey. When used in a complete composition in conjunction with a cellulosic polymer, the natural honey is preferably present at levels of from about 0.1% to about 25% by weight of the composition. More preferably, the composition comprises from about 0.1% to about 15%, more preferably still from about 0.1% to about 10% natural honey by weight of the composition.

Chelant

The honey composition, honey flavour composition and the composition of the present invention further comprise a chelant. Without wishing to be bound by theory, it is believed that the chelant acts to chelate the metal cofactor held within the quaternary structure of the cellulase enzyme present in the natural honey. As a result, the cellulase enzyme is partially denatured, thereby decreasing its enzymatic activity.

As used herein the term "chelant" includes compounds and materials that means a molecule containing two or more electron donor atoms that can form coordinate bonds to a single metal ion. The term "chelant" is understood to include the chelant as well as salts thereof. For example, the term "chelant" includes citric acid as well as its salt forms.

The most common and widely used chelants coordinate to metal atoms through oxygen or nitrogen donor atoms, or both. Other less common chelants coordinate through sulfur in the form of —SH (thiol or mercapto) groups. After the first coordinate bond is formed, each successive donor atom that binds creates a ring containing the metal atom. A chelant may be bidentate, tridentate, tetradentate, etc., depending upon whether it contains two, three, four, or more donor atoms capable of binding to the metal atom. See Kirk-Othmer Encyclopedia of Chemical Technology (4$^{th}$ ed. 2001).

The chelant may be soluble or insoluble in the natural honey as long as it is readily available for complexation with metal ions in the food. Various classes of chelant are suitable for use in the present invention. Non-limiting examples of these classes include polyphosphates (e.g., sodium tripolyphosphate, hexametaphosphoric acid, sodium acid pyrophosphate, sodium pyrophosphate, tetra sodium pyrophosphate, sodium hexametaphosphate, sodium metaphosphate); aminocarboxylic acids (e.g., ethylenediaminetetraacetic acid (EDTA), 1,2-bis(2-amino-phenoxy)ethane-N,N,N'N'-tetraacetic acid (EGTA), ethylenebis(oxyethylenenitrilo)-tetraacetic acid (BAPTA), N-(hydroxyethyl)-ethylenediaminetriacetic acid (HEDTA), diethylenetriaminepentaacetic acid (DTPA), N-dihydroxyethylglycine (2-HxG), ethylenebis(hydroxyphenylglycine) (EHPG), glutamic acid, aspartic acid, glycine, lysine); 1,3-diketones (e.g., acetylacetone, trifluoroacetylacetone, thenoyltrifluoroacetone, ascorbic acid); hydroxycarboxylic acids (e.g., tartaric acid, citric acid, malic acid, gluconic acid, ferulic acid, lactic acid, glucuronic acid); polyamines (e.g., dietheylenetriamine, triethylenetriamine); aminoalcohols (e.g., triethanolamine, N-hydroxyethylethylene-diamine, aminoethylethanolamine (AEEA); phenols (e.g., disulfopyrocatechol, chromotropic acid); aminophenols (e.g., oxinesulfonic acid); Schiff bases (e.g., disalicylaldehyde 1,2-propylenediimine); tetrapyrroles (e.g., tetraphenylporphin, phthalocyanine); silicates (aluminum calcium silicate, calcium silicate, sodium aluminosilicate sodium calcium aluminosilicate (hydrates), tricalcium silicate); sulfur compounds (e.g., potassium ethyl xanate, sodium diethyldithiocarbamate, diethyl dithiophosphoric acid, thiourea, magnesium sulfate); synthetic macrocyclic compounds (e.g., hexamethyl-[14]-4,11-dieneN$_4$, 2.2.2-cryptate); polymers (e.g., polyethyleneimines, polymethacryloylacetone, poly(p-vinylbenzyliminodiacetic acid)), phosphonic and bisphosphonic acids (e.g., nitrilotrimethylenephosphonic acid, ethylenediaminetetra-(methylenephosphonic acid), hydroxyethylidenediphosphonic acid).

In a preferred embodiment, the chelant is selected from the group comprising polyphosphates, aminocarboxylic acids, 1,3-diketones, hydroxycarboxylic acids and mixtures thereof. More preferably, the chelant is selected from the group comprising aminocarboxylic acids, 1,3-diketones, hydroxycarboxylic acids and mixtures thereof. More preferably still, the chelant is selected from the group comprising EDTA, phytic acid, citric acid, malic acid, tartaric acid, lactic acid, adipic acid, succinic acid, aspartic acid, glutamic acid, lysine, or mixtures thereof. In a further preferred embodiment, the chelant is EDTA, phytic acid, citric acid or mixtures thereof, more preferably EDTA, phytic acid or mixtures thereof.

The amount of chelant present in the honey composition, the honey flavour composition and the composition itself is dependant upon the amount of natural honey present and will further depend on the particular chelant or chelants (i.e. mixtures of chelating agents) selected. The chelant generally should be present at a level of from about 0.01% to about 5% by weight of natural honey, preferably from about 0.1% to about 3% by weight of natural honey. Where the chelant is selected from the group comprising EDTA, phytic acid, citric acid, malic acid, tartaric acid, lactic acid, adipic acid, succinic acid, aspartic acid, glutamic acid, lysine, and mixtures thereof, the chelant is preferably present at from about 0.01% to about 5% by weight of natural honey. Preferably, when the chelant is selected from EDTA, phytic acid or mixtures thereof, the chelant is present at from about 0.01 to about 1%, by weight of the natural honey.

Cellulosic Polymer

The compositions according to one embodiment of the present invention comprise a cellulosic polymer. The cellulosic polymer is generally used to thicken or structure the compositions of the present invention. As used herein, the term "cellulosic polymer" is a polymer comprising a cellulose monomer backbone wherein the cellulose monomers may optionally comprise chemically modified functionalities. Suitable non-limiting examples of chemical modification include hydroxyl functionality modification. Non limiting examples of cellulosic polymers for use herein include hydroxypropylmethylcellulose, hydroxyethylcellulose, methylcellulose, icrocrystalline cellulose, carboxymethylcellulose, ethylhydroxyethylcellulose, celluloseacetateptha-lalte, ethylcellulose, hydroxypropylcellulose and mixtures thereof and their commonly used salts. Preferably the cellulosic polymer comprises carboxymethylcellulosem and its commonly used salts.

The compositions according to the present invention preferably have sufficient cellulosic polymer to maintain the viscosity of the composition from about 50 cps to about 5000 cps, preferably from about 100 cps to about 1000 cps. As used herein, viscosity is measured at 25° C. using a Brookfields RVDV-II+ with cone 51 and sample cup at 10 rpm.

The compositions according to the present invention preferably comprise from about 0.1% to about 10% cellulosic polymer by weight of the composition, more preferably from about 0.1% to about 5% by weight of the composition.

The compositions of the present invention may optionally further comprise additional thickeners provided that the cellulosic polymer is also present. Suitable non-limiting examples of thickeners suitable for use herein in conjunction with the cellulosic polymer include natural polymers, polymeric cellulose derivatives, polyvinyl pyrrolidones (PVPs), dextran polymers, polyethylene oxide polymers including Polyox-600, thermoreversible polymers, ionic responsive polymers, copolymers of polymethyl vinyl ether and maleic anhydride, and mixtures thereof. Polymeric cellulose derivatives and thermoreversible polymers are preferred.

Specific nonlimiting examples of natural polymers suitable for use as a viscosity building polymer herein include icroc gums, tragacanth gums, agar polymers, xanthan gums, copolymers of alginic acid and sodium alginate, chitosan polymers, pectins, carageenans, pollulan polymers, modified starches, and mixtures thereof.

Specific nonlimiting examples of ionic responsive polymers suitable for use as a viscosity building polymer herein include gelrite, gellan gum, Kelcogel F, and mixtures thereof.

Specific nonlimiting examples of copolymers of polymethyl vinyl ether and maleic anhydride suitable for use as viscosity building polymer herein include such copolymers sold under the Gantrez tradename including Gantrez S and Gantrez MS type copolymers.

Known viscosity building polymers suitable for use herein are selected from the group consisting of carboxypolymethylene, carboxyvinyl polymers, homopolymers of acrylic acid crosslinked with an allyl ether of pentaerythritol, homopolymers of acrylic acid crosslinked with an allyl ether of sucrose, homopolymers of acrylic acid crosslinked with divinyl glycol, and mixtures thereof.

Carrier

The honey flavour composition of the present invention comprises the honey composition and a carrier. The carrier may be any inert vehicle known to those skilled in the art suitable for use as a carrier for a flavour ingredient. Such carriers are suitable for human ingestion and are typically selected such that the flavour ingredient, in this case natural honey, is soluble or miscible in the carrier. Alternatively, the carrier may be selected such that the natural honey is emulsified within the carrier. Non-limiting examples of carriers suitable for use in the honey flavour compositions of the present invention include but not limited to propylene glycol, polyethylene glycol, ethanol, water, or mixtures thereof. Preferably, the carrier comprises from about 30% to about 95% by weight of the honey flavour composition.

Compositional Form

The present invention provides compositions comprising natural honey, a chelant and a cellulosic polymer. The compositions according to this embodiment may be in the form of a medicament, a food, a beverage or a ready-made ingredient pre-mix for use in one of the foregoing categories. Preferably, the composition is in the form of a medicament. The medicament may be formulated as a syrup, a unit-dosage liquid filled capsule, a centre-filled throat drop and the like, preferably a syrup.

Where the composition is a medicament, the composition preferably comprises a pharmaceutical active. The pharmaceutical active can be included in the compositions as an individual active ingredient or as a combination of active ingredients. The pharmaceutical active is preferably especially effective in the prevention and treatment of cold and influenza-like symptoms. The pharmaceutical active is included in the pharmaceutical compositions of the present invention at a level of from about 0.01 to about 60%, preferably from about 0.1% to about 20%, more preferably still from about 0.1% to about 10% by weight of the composition.

Nonlimiting examples of active ingredients suitable for use herein include those active ingredients that are pharmacologically classified as antitussives, antihistaminics, non-sedating antihistamines, decongestants, expectorants, mucolytics, analgesics, antipyretics, anti-inflammatory agents, local anesthetics, and mixtures thereof. These active ingredients are more fully described in J. G. Hardman, The Pharmacologic Basis of Therapeutics, Ninth Edition, McGraw-Hill, New York, 1995. Preferably, the pharmaceutical active is selected from the group comprising antitussives, decongestants, antihistaminics, expectorants, mucolytics or mixtures thereof. More preferably, the pharmaceutical active is selected from the group comprising antitussives, expectorants, mucolytics, decongestants or mixtures thereof.

Specific nonlimiting examples of antitussives suitable for use herein include those antitussive compounds which are especially effective in treating symptoms of the common cold such as fits of coughing. Suitable specific antitussives include codeine, dextromethorphan, dextrorphan, hydrocodone, noscapine, oxycodone, pentoxyverine, and mixtures thereof. Dextromethorphan is a preferred antitussive. As used herein, "dextromethorphan" means racemethorphan, (+−)-3-Methoxy-17-methylmorphinan, dl-cis-1,3,4,9,10,10a-hexahydro-6-methoxy-11-methyl-2H-10,4a-iminoethanophenanthrene, and pharmaceutical salts thereof including dextromethorphan hydrobromide. Dextromethorphan and its pharmaceutically-acceptable salts are more fully described in U.S. Pat. No. 5,196,436. Specific nonlimiting examples of antihistaminics suitable for use herein include acrivastine, azatadine, brompheniramine, brompheniramine maleate, chlorpheniramine, chlorpheniramine maleate, clemastine, cyproheptadine, dexbrompheniramine, dimenhydrinate, diphenhydramine, diphenhydramine hydrochloride, hydroxyzine, meclizine, pheninamine, phenyltoloxamine, promethazine, pyrilamine, pyrilamine maleate, tripelennamine, triprolidine, doxylamine, doxylamine succinate, and mixtures thereof.

Specific non limiting examples of non-sedating antihistamines suitable for use herein include astemizole, cetirizine, ebastine, fexofenadine, loratidine, terfenadine, and mixtures thereof. Specific nonlimiting examples of decongestants suitable for use herein include phenylpropanolamine, pseudoephedrine, pseudoephedrine hydrochloride, pseudoephedrine sulfate, ephedrine, phenylephrine, phenylephrine hydrochloride, and mixtures thereof, Specific non limiting examples of expectorants suitable for use herein include ammonium chloride, guafenesin, ipecac fluid extract, potassium iodide, and mixtures thereof, Specific nonlimiting examples of mucolytics suitable for use herein include acetylcysteine, ambroxol, bromhexine, and mixtures thereof. Specific nonlimiting examples of analgesics, anti-pyretics, and anti-inflammatory agents suitable for use herein include acetaminophen, aspirin, sodium salicylate, salicylamide, diclofenac, diflunisal, etodolac, fenoprofen, flurbiprofen, ibuprofen, ketoprofen, ketorolac, nabumetone, naproxen, piroxicam, caffeine, ketorolac, indomethacin, meclofenamic acid, COX-2 inhibitors such as valdecoxib, celecoxib and rofecoxib, and mixtures thereof.

Optional Ingredients

Water may be used in compositions of the present invention. In the present invention the maximum level of water is about 10%, preferably from about 1% to about 10%, more preferably from about 5% to about 10% and more preferably still from about 5% to about 8% by weight of the composition.

The compositions and honey flavour compositions of the present invention may further comprise a buffer or mixtures of buffering agents. Non-limiting examples of suitable buffering agents for use herein include basic buffers with pKa of from 8 to 11 including triethanolamine, tromethamine, salts of amino acids including alkaline salts of glycine, glycylglycine, glutamine or other amino acids, alkaline salts of phosphate, carbonate or mixtures thereof. The buffers provide compositional resistance to pH changes upon dilution of the composition with saliva within the pH range of 8 to 10.

Sweeteners may optionally be added to the compositions and honey flavour compositions of the present invention. Suitable flavours for use herein include aspartame, saccharin and its salts, Sucralose™ (sold by the McNeil Specialty Products Co., New Brunswick, N.J.); Prosweet™ (sold by the Virginia Dare Extract Co., New York, N.Y.); Magnasweet™ (sold by MAFCO Worldwide Corp., Licorice Division, Camden, N.J.); ammonium glycyrrhizinate and its salts, Talin™ (thaumatin) and its diluted products, such as Talin GA90, (sold by the Talin Food Company, Birkenhead, England); and Acesulfame K, or mixtures thereof.

Other flavoring agents that may be used in the compositions and honey flavour compositions of the present invention include anise, oil of peppermint, oil of clove, eucalyptus, lemon, lime, honey lemon, red fruit, mint, grapefruit, orange, cherry cola or mixtures thereof.

The compositions and honey flavour compositions of the present invention may further comprise sensory agents. Suitable non-limiting examples of sensory agents useful herein are sensory agents selected from the group consisting of coolants, salivating agents, warming agents or mixtures thereof. When present, these agents are preferably present in the compositions at a level of from about 0.001% to about 10%, preferably from about 0.1% to about 1%, by weight of the composition.

Non-limiting examples of suitable cooling agents include carboxamides, menthols, thymol, camphor, phenol, eucalyptus oil, benzyl alcohol, salicyl alcohol, ethanol, clove bud oil, and hexylresorcinol, ketals, diols, and mixtures thereof. Preferred warming agents include thymol, camphor, capsicum, phenol, benzyl alcohol, salicyl alcohol, ethanol, clove bud oil, and hexylresorcinol, nicotinate esters such as benzyl nicotinate, ketals, diols, capsicum, and mixtures thereof.

Preferred coolants include the paramenthan carboxyamide agents such as N-ethyl-p-menthan-3-carboxamide (WS-3 supplied by Sterling Organics), taught by U.S. Pat. No. 4,136,163, issued Jan. 23, 1979, to Watson et al. Preferred coolants are the paramenthan carboxyamide agents such as N-ethyl-p-menthan-3-carboxamide. Another preferred paramenthan carboxyamide agent is N,2,3-trimethyl-2-isopropylbutanamide, known as "WS-23", or mixtures of WS-3 and WS-23.

Additional preferred coolants are selected from the group consisting of menthol, 3-1-menthoxypropane-1,2-diol, known as TK-10 supplied by Takasago Perfumery Co., Ltd., Tokyo, Japan, menthone glycerol acetal known as MGA, manufactured by Haarmann and Reimer, menthyl lactate known as Frescolat® manufactured by Haarmann and Reimer, or mixtures thereof.

Process of Manufacture

The present invention further provides for a process of manufacturing a composition comprising natural honey comprising the step of mixing a chelant with natural honey and optionally a carrier. The chelant may be added neat to the natural honey and mixed, or added as a solution in water or similar diluent. The natural honey and chelant are mixed together using mixing techniques known to those skilled in the art, non-limiting examples of which include stirring, extruder mixing, shaking and the like. The mixing step must be sufficient to ensure appropriate distribution of the chelant in the natural honey so as to effectively inhibit the cellulase present in the natural honey.

The process of the present invention may preferably include an additional step in which the natural honey is heated either before or after the chelant is mixed with the natural honey, preferably after the mixing of the chelant with the natural honey. The heating step generally involves heating the natural honey or natural honey and chelant mix to a temperature of from about 90° C. to about 140° C., preferably from about 100° C. to about 120° C. The heating step preferably has a duration of from about 1 minute to about 60 minutes, preferably about 1 minute to about 30 minutes and more preferably from about 1 minute to about 10 minutes. Without wishing to be bound by theory, it is believed that the heating step denatures the cellulase enzyme present in the natural honey, thereby deactivating it. The cellulase enzyme however is quite robust, and apparently due to the presence of a central metal cofactor, able to renature over a period of time even after exposure to high temperature. The combination of heat treatment either in the presence of a chelant or with subsequent addition of the chelant results in the central metal cofactor being exposed and more readily chelated by the chelant. Removal of the metal cofactor inhibits the re-folding of the cellulase enzyme, resulting in a more efficient and permanent inhibition of the cellulase enzyme in the natural honey.

The heating step may be carried out using processes and equipment known to those skilled in the art, non-limiting examples of which include autoclaving, pressurized heating vessels, heating vessels with mixing capability. Preferably, the heating step is undertaken in an autoclave with stirring capability or other suitable jacketed pressurized mixing vessel.

EXAMPLES

| Honey Composition | 1 | 2 | 3 | 4 |
|---|---|---|---|---|
| | Percentage (%) | | | |
| EDTA | 0.001 | 0.01 | 0.1 | 1 |
| Honey containing cellulose enzyme | 99.999 | 99.99 | 99.9 | 99 |
| Total | 100 | 100 | 100 | 100 |

Manufacturing method: Heated to 110° C.-120° C. for 5 to 30 minutes with or without a pressurised mixing vessel.

| Honey Composition | 5 | 6 | 7 | 8 |
|---|---|---|---|---|
| | Percentage (%) | | | |
| EDTA | 0.005 | 0.05 | 0.5 | 2 |
| Honey containing cellulose enzyme | 99.995 | 99.95 | 99.5 | 98 |
| Total | 100 | 100 | 100 | 100 |

Manufacturing method: Mixing for 5-30 minutes

| Honey Flavour Composition | 9 | 10 | 11 | 12 |
|---|---|---|---|---|
| | Percentage (%) | | | |
| EDTA | 0.001 | 0.01 | 0.1 | 1 |
| Honey containing cellulose enzyme | 50 | 50 | 50 | 50 |
| Propylene glycol | 49.999 | 49.99 | 49.9 | 49 |
| Total | 100 | 100 | 100 | 100 |

-continued

Manufacturing method: Heated to 110° C.-120° C. for 5 to 30 minutes with or without a pressurised mixing vessel.

| Honey Flavour Composition | 13 | 14 | 15 | 16 |
|---|---|---|---|---|
| | | Percentage (%) | | |
| EDTA | 0.001 | 0.01 | 0.1 | 1 |
| Honey containing cellulose enzyme | 50 | 50 | 50 | 50 |
| Propylene glycol | 49.999 | 49.99 | 49.9 | 49 |
| Total | 100 | 100 | 100 | 100 |

Manufacturing method: Mixing for 5-30 minutes

| Cough & cold Formulations | 17 % w/v | 18 % w/v | 19 % w/v | 20 % w/v | 21 % w/v |
|---|---|---|---|---|---|
| DEXTROMETHORPHAN HBR | 0.133 | 0.133 | 0.000 | 0.133 | 0.000 |
| GUAIFENESIN | 1.333 | 0.000 | 1.333 | 0.000 | 1.333 |
| CARBOXYMETHYLCELLULOSE SODIUM | 0.400 | 0.450 | 0.500 | 1.000 | 2.000 |
| POLYETHYLENE OXIDE | 0.100 | 0.100 | 0.100 | 0.100 | 0.100 |
| SUCROSE | 37.000 | 37.000 | 37.000 | 37.000 | 37.000 |
| PROPYLENE GLYCOL | 5.20 | 5.20 | 5.20 | 5.20 | 5.20 |
| ALCOHOL | 5.00 | 5.00 | 5.00 | 5.00 | 5.00 |
| SODIUM SACCHARIN | 0.075 | 0.075 | 0.075 | 0.075 | 0.075 |
| SODIUM BENZOATE | 0.100 | 0.100 | 0.100 | 0.100 | 0.100 |
| SODIUM CITRATE DIHYDRATE | 0.522 | 0.522 | 0.522 | 0.522 | 0.522 |
| CITRIC ACID ANHYDROUS | 0.338 | 0.338 | 0.338 | 0.338 | 0.338 |
| PEG-40 STEARATE | 0.300 | 0.300 | 0.300 | 0.300 | 0.300 |
| LEVOMENTHOL SYNTHETIC | 0.020 | 0.020 | 0.020 | 0.020 | 0.020 |
| HONEY FLAVOUR of Ex. 11 | 0.50 | 1.00 | 3.00 | 5.00 | 10.00 |
| MENTHOXYPROPANEDIOL (TK10) | 0.040 | 0.040 | 0.040 | 0.040 | 0.040 |
| VERVEINE FLAVOUR 97445-73 | 0.020 | 0.020 | 0.020 | 0.020 | 0.020 |
| WATER PURIFIED EP TO VOLUME | 100% w/v | 100% w/v | 100% w/v | 100% w/v | 100% w/v |

Manufacturing method: Build a viscose liquid by adding water to Cellulose gum and polyethylene oxide.
Add Sucrose
Dissolve the buffer components in water and add to the mix
Add propylene glycol
Add Actives, PEG-40 sterate, alcohol and flavours.

| Multi Symptom Relief Formulation | 22 % w/v | 23 % w/v | 24 % w/v | 25 % w/v |
|---|---|---|---|---|
| PSEUDOEPHEDRINE | 30 mg | 30 mg | 0.00 | 30 mg |
| ACETAMINOPHEN | 500 mg | 0.00 | 500 mg | 500 mg |
| DEXTROMETHORPHAN HBR | 0.133 | 0.133 | 0.000 | 0.000 |
| GUAIFENESIN | 1.333 | 0.000 | 1.333 | 0.000 |
| HYDROXYPROPYL METHYLCELLULOSE | 0.50 | 0.00 | 0.00 | 0.00 |
| HYDROXYETHYLCELLULOSE | 0.00 | 1.00 | 0.00 | 0.00 |
| HYDROXYBUTYLCELLULOSE | 0.00 | 0.00 | 1.50 | 1.50 |
| POLYETHYLENE OXIDE | 0.100 | 0.100 | 0.100 | 0.100 |
| SUCROSE | 37.000 | 37.000 | 37.000 | 37.000 |
| PROPYLENE GLYCOL | 5.20 | 5.20 | 5.20 | 5.20 |
| ALCOHOL 96% | 5.00 | 5.00 | 5.00 | 5.00 |
| SODIUM SACCHARIN | 0.075 | 0.075 | 0.075 | 0.075 |
| SODIUM BENZOATE | 0.100 | 0.100 | 0.100 | 0.100 |
| SODIUM CITRATE DIHYDRATE | 0.522 | 0.522 | 0.522 | 0.522 |
| CITRIC ACID ANHYDROUS | 0.338 | 0.338 | 0.338 | 0.338 |
| PEG-40 STEARATE | 0.300 | 0.300 | 0.300 | 0.300 |
| LEVOMENTHOL SYNTHETIC | 0.020 | 0.020 | 0.020 | 0.020 |
| HONEY FLAVOUR of Example 15 | 1.00 | 5.00 | 10.00 | 10.00 |
| MENTHOXYPROPANEDIOL (TK10) | 0.040 | 0.040 | 0.040 | 0.040 |
| VERVEINE FLAVOUR 97445-73 | 0.020 | 0.020 | 0.020 | 0.020 |
| WATER PURIFIED EP TO VOLUME | 100% w/v | 100% w/v | 100% w/v | 100% w/v |

Manufacturing method: Build a viscose liquid by adding water to Cellulose gum and polyethylene oxide.
Add Sucrose
Dissolve the buffer components in water and add to the mix
Add propylene glycol
Add Actives, PEG-40 sterate, alcohol and flavours.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the inventions. It is therefore intended to cover in the appended claims all such changes and modifications that are within the scope of this invention.

What is claimed is:

1. A composition comprising:
   a. a honey flavour composition consisting essentially of:
      honey comprising at least one cellulase enzyme; and
      a chelant selected from the group consisting of polyphosphates, aminocarboxylic acids, hydroxycarboxylic acids, polyamines, phenols, Schiff bases silicates, sulfur compounds, synthetic macrocyclic compounds, polymers, phosphonic and biphosphonic acids or mixtures thereof;
   b. a cellulosic polymer;
      wherein the composition is a medicinal preparation formulated as a syrup; and
      wherein a loss of viscosity associated with the degradation of the cellulosic polymer is less than about 50%.

2. The composition according to claim 1 wherein the honey flavour composition contains from 0.01% to 5% chelant.

3. The composition according to claim 2 wherein the honey flavour compositions contains from 0.1% to 3% chelant by weight.

4. The composition according to claim 1 wherein the chelant is an aminocarboxylic acid selected from the group consisting of EDTA, aspartic acid, glutamic acid, lysine, or mixtures thereof.

5. The composition according to claim 4 wherein the chelant is EDTA.

6. The composition according to claim 1 further comprising a carrier in which the honey is soluble.

7. The composition according to claim 1 wherein the honey flavour composition contains from 5% to 70% honey.

8. The composition according to claim 6 wherein the carrier is selected from the group comprising propylene glycol, polyethylene glycol, ethanol, water or mixtures thereof.

9. A composition comprising;
   a. from about 0.1% to about 25%, by weight of the composition, honey comprising at least one cellulase enzyme;
   b. from 0.01% to 5%, by weight of the honey, chelant wherein the chelant is selected from the group consisting of EDTA, phytic acid, citric acid, malic acid, tartaric acid, lactic acid, adipic acid, succinic acid, aspartic acid, glutamic acid, lysine, or mixtures thereof; and
   a. from about 0.1% to 10%, by weight of the composition, cellulosic polymer;
      wherein the composition is a medicinal preparation formulated as a syrup; and
      wherein the composition has a viscosity from about 100 cps to about 1000 cps.

10. The composition according to claim 9 wherein the composition comprises from 0.1% to 15% honey by weight of the composition.

11. The composition according to claim 10 wherein the composition comprises from 0.1% to 10% honey by weight of the composition.

12. The composition according to claim 9 wherein the chelant is EDTA.

13. The composition according to claim 9 wherein the composition comprises from 0.1% to 3% chelant by weight of the honey.

14. The composition according to claim 13 wherein the composition comprises from 0.01% to 1% by weight of the honey.

15. The composition according to claim 9 wherein the composition comprises from 0.1% to 5% of the cellulosic polymer by weight of the composition.

16. The composition according to claim 9 wherein the cellulosic polymer comprises hydroxypropylmethylcellulose, hydroxyethylcellulose, methylcellulose, icrocrystalline cellulose, carboxymethylcellulose and its salts, ethylhydroxyethylcellulose, celluloseacetatepthalalte, ethylcellulose, hydroxypropyl-cellulose, salts thereof or mixtures thereof.

17. The composition according to claim 16 wherein the cellulosic polymer comprises carboxymethylcellulose and its salts.

18. A process for the manufacture of a composition comprising honey comprising at least one cellulose enzyme; the process comprising the step of mixing a chelant with honey and optionally a carrier.

19. The process according to claim 18 further comprising the step of heating said honey or the honey and chelant mixture to a temperature of from 50° C. to 140° C.

20. The process according to claim 19 wherein the honey or the honey and chelant mixture is heated to a temperature of from 90° C. to 130° C.

21. The process according to claim 20 wherein said heating step occurs after the chelant has been mixed with the honey.

22. The process according to claim 19 wherein said heating step has a duration of from 1 minute to 60 minutes.

23. The process according to claim 22 wherein said heating step has a duration of from 1 minute to 30 minutes.

24. The process according to claim 19 wherein said heating step is carried out in an autoclave or suitable jacketed pressurized mixing vessels with mixing capability.

25. The process according to claim 18 wherein the chelant is selected from the group comprising polyphosphates, aminocarboxylic acids, 1,3-diketones, hydroxycarboxylic acids, polyamines, phenols, Schiff bases, silicates, sulfur compounds, synthetic macrocyclic compounds, polymers, phosphonic and biphosphonic acids and mixtures thereof, preferably polyphosphates, aminocarboxylic acids, 1,3-diketones, hydroxycarboxylic acids or mixtures thereof.

26. The process according to claim 25 wherein the chelant is selected from the group comprising EDTA, phytic acid, citric acid, malic acid, tartaric acid, lactic acid, adipic acid, succinic acid, aspartic acid, glutamic acid, lysine, or mixtures thereof.

27. The process according to claim 26 wherein the chelant is selected from the group comprising EDTA, phytic acid or mixtures thereof.

28. The process according to claim 18 wherein from 0.01% to 5% by weight of the honey is mixed with the honey.

29. The honey flavour composition of claim 1 further comprising a pharmaceutical active selected from the group consisting of antitussives, antihistaminics, non-sedating antihistamines, decongestants, expectorants, mucolytics, analgesics, antipyretics, anti-inflammatory agents, local anesthetics, and mixtures thereof.

30. A composition comprising:
    a. honey comprising at least one cellulase enzyme;
    b. from about 0.01% to about 1%, by weight of the honey, chelant selected from EDTA, phytic acid and mixtures thereof;
    c. a carrier in which the honey is soluble or miscible in the carrier;
    d. from about 0.1% to about 5%, by weight of the composition, carboxymethylcellulose and its salts;
    e. a pharmaceutical active selected from the group consisting dextromethorphan, guaifenesin, pseudophedrine, acetaminophen, phenylephrine and combinations thereof;
        wherein the composition is a medicinal preparation formulated as a syrup;
        wherein the composition has a viscosity from about 100 cps to about 1000 cps; and
        wherein a loss of viscosity associated with the degradation of the cellulosic polymer is less than about 30%.

31. The honey flavor composition according to claim 30 wherein the carrier is selected from the group consisting of polyethylene glycol, propylene glycol, water, and combinations thereof.

* * * * *